United States Patent
Allen et al.

(10) Patent No.: US 6,831,206 B2
(45) Date of Patent: Dec. 14, 2004

(54) SERINE O-ACETYTRANSFERASE

(76) Inventors: Stephen M. Allen, 2225 Rosewood Dr., Wilmington, DE (US) 19810; Saverio C. Falco, 1902 Miller Rd., Arden, DE (US) 19810; Mitchell C. Tarczynski, 2115 S. 4th St., West Des Moines, IA (US) 50265

( * ) Notice: Subject to any disclaimer, the term of this patent is extended or adjusted under 35 U.S.C. 154(b) by 0 days.

(21) Appl. No.: 10/151,832

(22) Filed: May 21, 2002

(65) Prior Publication Data

US 2003/0008368 A1 Jan. 9, 2003

Related U.S. Application Data

(60) Provisional application No. 60/292,411, filed on May 21, 2001.

(51) Int. Cl.$^7$ ............... A01H 1/00; C07H 21/04; C07K 14/415; C12N 5/14; C12N 9/00
(52) U.S. Cl. ............... 800/295; 435/6; 435/69.1; 435/468; 435/419; 435/252.3; 435/320.1; 530/370; 536/23.6; 800/278
(58) Field of Search ............... 435/6, 69.1, 70.1, 435/91.4, 468, 183, 410, 419, 252.3, 320.1; 530/370; 536/23.2, 23.6; 800/278, 295

(56) References Cited

FOREIGN PATENT DOCUMENTS

| | | |
|---|---|---|
| WO | WO 00/04167 A2 | 1/2000 |
| WO | WO 00/36127 A1 | 6/2000 |

OTHER PUBLICATIONS

Frank W. Smith et al., "Plant Members of a Family of Sulfate Transporters Reveal Functional Subtypes," Proc. Natl. Acad. Sci., vol. 92:9373–9377, Sep. 1995.

Anelo Bolchi et al., "Coordinate Modulation of Maize Sulfate Permease and ATP Sulfurylase MRNAS in Response to Variations in Sulfer Nutritional Status: Stereospecific Down–Regulation by L–Cysteine ," Plant Molecular Biology, vol. 39:527–537, 1999.

Hildegard E. Arz et al., "A CDNA for Adenylyl Sulphate (APS)–Kinase from Arabidopsis Thaliana," Biochimica ET Biophysica ACTA, vol. 1218:447–452, 1994.

Amit Setya et. al., "Sulfate Reduction in Higher Plants: Molecular Evidence for a Novel 5'–Adenylylsulfate Reductase," Proc. Natl. Acad. Sci., vol. 93:13383–13388, Nov. 1996.

Keiko Yonekura–Sakakibara et al., "Molecular Characterization of Tobacco Sulfite Reductase: Enzyme Purification, Gene Cloning, and Gene Expression Analysis," J. Biochem., vol. 124:615–621, 1998.

Kazuki Saito et. al., "Molecular Cloning and Characterization of a Plant Serine Acetyltransferase Playing a Regulatory Role in Cysteine Biosynthesis from Watermelon," The Journal of Biological Chemistry, vol. 270:16321–16326, Jul. 7, 1995.

National Center for Biotechnology Information Database, Accession No. AAF19000, General Identifier No. 6601494, Dec. 19, 1999, Serine Acetyltransferase [Allium CEPA].

National Center for Biotechnology Information Database, Accession No. A57478, General Identifier No. 1361979, Jun. 20, 2000, Serine O–Acetyltransferase (EC 2.3.1.30)–Watermelon.

National Center for Biotechnology Information Database, Accession No. BAA93050, General Identifier No. 7384806, Nov. 23, 2000, Serine Acetyltransferase [Allium Tuberosum].

National Center for Biotechnology Information Database, Accession No. S71207, General Identifier No. 2146774, May 5, 2000, Serine O–Acetyltransferase (EC 2.3.1.30) SAT–52–Arabidopsis Thaliana.

Yasuomi Urano et. al., "Molecular Cloning and Functional Characterization of CDNAS Encoding Cysteine Synthase and Serine Acetyltransferase that may be Responsible for High Cellular Cysteine Content in Allium Tuberosum, "Gene, vol. 257:269–277, 2000.

Bogdanova et al., "Cysteine synthesis in plants: protein—protein interactions of serine acetyltransferase from *Arabidopsis thaliana*," The Plant Journal, 1997, 11(2), 251–262.

*Primary Examiner*—Phuong T. Bui
(74) *Attorney, Agent, or Firm*—Morgan & Finnnegan, L.L.P.

(57) ABSTRACT

This invention relates to an isolated nucleic acid fragment encoding a serine O-acetyltransferase. The invention also relates to the construction of a recombinant DNA construct encoding all or a portion of the serine O-acetyltransferase, in sense or antisense orientation, wherein expression of the recombinant DNA construct results in production of altered levels of the serine O-acetyltransferase in a transformed host cell.

11 Claims, 2 Drawing Sheets

| | | |
|---|---|---|
| SEQ ID NO:3 | 1 | MTAGQL--LRTEPSAQPQRVRHSTPPA-ALQADIVPSYPPESDGDESWVWSQIKAEARR |
| SEQ ID NO:5 | 1 | MPAGQQPPAREPDGGDSNHHPHPPPTPALPSEVVPAYPPPESEDDESWVWTQIKAEARR |
| SEQ ID NO:8 | 1 | MPCSTVP----------------------------FPTFPPPESESDESWVWNQIKAEARR |
| SEQ ID NO:9 | 1 | M------PPAGELRHQSPSKEKLSSVTQSDEAEAASAAISAAAADAEAAGLWTQIKAEARR 60 |
| SEQ ID NO:3 | 58 | DADAEPALASFLYATVLSHASLDRSLAFHLANKLCSSTLLSTLLYDLFVASLAEHPSVRA |
| SEQ ID NO:5 | 61 | DADAEPALASFLYATVLSHASLDRSLAFHLANKLCSSTLLSTLLYDLFLASLTAHPSLRA |
| SEQ ID NO:8 | 34 | DAESEPALASYLYSTIISHPSLARSLSFHLANKLCSSTLLSTLSLYDLFLNALSTFPTILS |
| SEQ ID NO:9 | 56 | DAEAEPALASYLYSTILSHSSLERSISFHLGNKLCSSTLLSTLLYDLFLNTFSSDPSLRN 120 |
| SEQ ID NO:3 | 118 | AAVADLIAARSRDPACAGEFAHCLLNYKGFLAVQAHRVAHVIWAQGRRALALALQSRVAEV |
| SEQ ID NO:5 | 121 | AVVADLLAARARDPACVGFSHCLLNYKGFLAIQAHRVAHVLWAQNRRPLALALQSRVADV |
| SEQ ID NO:8 | 94 | ATVADLIAARHRDPACIGFSHCLLNFKGFIAVQTQRIAHVLWSQSRRPLALALHSRVADV |
| SEQ ID NO:9 | 116 | ATVADLRAARVRDPACISFSHCLLNYKGFLAIQAHRVSHKLWTQSRKPLALALHSRISDV 180 |
| SEQ ID NO:3 | 178 | FAVDIHPAATVGRGILLDHATGVVVGETAVVGDNVSILHHVTLGGTGKAVGDRHPKIGDG |
| SEQ ID NO:5 | 181 | FAVDIHPAAVVGKAILLDHATGVVIGETAVVGDNVSILHHVTLGGTGKAVGDRHPKIGDG |
| SEQ ID NO:8 | 154 | LSVDIHPAARIGKGILLDHATGVVIGETAVIGNNVSILHHVTLGGTGKAGGDRHPKIGDG |
| SEQ ID NO:9 | 176 | FAVDIHPAAKIGKGILLDHATGVVVGETAVIGNNVSILHHVTLGGTGKACGDRHPKIGDG 240 |

FIG. 1A

```
                        ************ *** ****** *    ************* * ************
SEQ ID NO:3      238    VLIGAGATVLGNVRIGAGAKVGAGSVVLIDVPPRSTAVGNPARLIGGKKGE----EVMPG
SEQ ID NO:5      241    VLIGAGATILGNVMIGAGAKVGAGSVVLIDVPARSTAVGNPARLIGGRKGESDKDEDMPG
SEQ ID NO:8      214    VLIGAGATILGNIRIGAGAKIGAGSVVLIDVPPRTTAVGNPARLIGG-KEKPSMHEDVPG
SEQ ID NO:9      236    CLIGAGATILGNVKIGAGAKVGAGSVVLIDVPCRGTAVGNPARLVGGKEKPTIHDEECPG
                 241                                                              300

*********** **** *
SEQ ID NO:3      294    ESMDHTSFIQQWSDYII  310
SEQ ID NO:5      301    ESMDHTSFIRQWSDYTI  317
SEQ ID NO:8      273    ESMDHTSFISEWSDYII  289
SEQ ID NO:9      296    ESMDHTSFISEWSDYII  312
                 301                       317
```

FIG. 1B

SEQUENCE LISTING

<160> NUMBER OF SEQ ID NOS: 9

<210> SEQ ID NO 1
<211> LENGTH: 1308
<212> TYPE: DNA
<213> ORGANISM: Zea mays

<400> SEQUENCE: 1

```
ccgcacaccc caccggccgg ccacataggc cccgacggcg actcgaagat gacggccggg      60
cagcttctgc gcaccgagcc atcagcccag ccccagcggg tgcgccacag caccccgccg     120
gcggcactcc aagcagacat cgtgccgtcg tacccgccgc ccgagtcgga cggtgacgag     180
tcgtgggtct ggtcccagat caaggcggag gcgcggcgcg acgcggacgc ggagccggcg     240
ctggcctcct tcctctacgc gacggtgctg tcgcacgcgt ccctggaccg gtccctggcc     300
ttccacctgg ccaacaagct gtgctcctcc acgctgctgt cgacgctcct ctacgacctc     360
ttcgtggcgt cgctcgcgga gcacccgtcc gtccgcgcgg cggcggtggc cgacctgatc     420
gccgcgcggt cgcgggaccc ggcctgcgcg ggcttcgcgc actgcctcct caactacaag     480
gggttcctgg ccgtgcaggc gcaccgcgtg gcgcacgtgc tgtgggcgca gggccggcgc     540
gcgctggcgc tggcgctcca gtcccgcgtc gccgaggtct tcgccgtgga catccacccg     600
gccgccaccg tcggcagggg catcctgctc gaccacgcca cgggcgtcgt cgtcggggag     660
acggccgtcg tgggcgacaa cgtctccata ctccaccacg tgacgctggg cggcaccggc     720
aaggcggtgg gcgaccggca ccccaagatc ggggacggcg tgctcatcgg cgccggcgcg     780
accgtcctcg gaaacgtcag gatcggcgcc ggcgccaagg tcggcgccgg gtccgtcgtg     840
ctcatcgacg tgccgcccag gagcaccgcc gtggggaacc ccgccaggct gatcggcggg     900
aagaagggcg aggaggtgat gccgggggag tccatggacc acacctcctt catacagcag     960
tggtcggact acatcatttg agcccgcaag ctagaaaaaa aaagagctcg tcttgctact    1020
gttgttatac tgctgttgcg ttttctgtgt atgtgcgtgg atgtgttagc tgtatgctct    1080
tgttccagtg aggtgaaccg tggacatgct ggtgtggtgt ccagaaagat atgctcaaag    1140
ttcgctctgt aattttcgaa gcagatgaac tgtgttacta cttttttactc tagtaaaaac    1200
tgtttctttg gctcaaaaaa aaaaaaaaaa aaaaaaaaaa aaaaaaaaaa aaaaaaaaaa    1260
aaaaaaaaaa aaaaaaaaaa aaaaaaaaaa aaaaaaaaa aaaaaaaa                  1308
```

<210> SEQ ID NO 2
<211> LENGTH: 1197
<212> TYPE: DNA
<213> ORGANISM: Zea mays

<400> SEQUENCE: 2

```
ggcgctgtgc gagccacacc gcccgcacac cccaccggcc ggccacatag gccccgacgg      60
cgactcgaag atgacggccg gcagcttctg cgcaccgagc catcagccca gccccagcg     120
ggtgcgccac agcaccccgc cggcggcact ccaagcagac atcgtgccgt cgtacccgcc     180
gcccgagtcg gacggtgacg agtcgtgggt ctggtcccag atcaaggcgg aggcgcggcg     240
cgacgcggac gcggagccgg cgctggcctc cttcctctac gcgacggtgc tgtcgcacgc     300
gtccctggac cggtccctgg ccttccacct ggccaacaag ctgtgctcct ccacgctgct     360
gtcgacgctc ctctacgacc tcttcgtggc gtcgctcgcg gagcacccgt ccgtccgcgc     420
ggcggcggtg gccgacctga tcgccgcgcg gtcgcgggac ccggcctgcg cgggcttcgc     480
gcactgcctc ctcaactaca aggggttcct ggccgtgcag gcgcaccgcg tggcgcacgt     540
gctgtgggcg cagggccggc gcgcgctggc gctggcgctc cagtcccgcg tcgccgaggt     600
cttcgccgtg gacatccacc cggccgccac cgtcggcagg ggcatcctgc tcgaccacgc     660
cacgggcgtc gtcgtcgggg agacggccgt cgtgggcgac aacgtctcca tactccacca    720
```

-continued

```
cgtgacgctg ggcggcaccg gcaaggcggt gggcgaccgg cacccccaaga tcggggacgg    780 cgtgctcatc ggcgccggcg cgaccgtcct cggaaacgtc aggatcggcg ccggcgccaa    840
ggtcggcgcc gggtccgtcg tgctcatcga cgtgccgccc aggagcaccg ccgtggggaa    900
ccccgccagg ctgatcggcg ggaagaaggg cgaggaggtg atgccggggg agtccatgga    960
ccacacctcc ttcatacagc agtggtcgga ctacatcatt tgagcccgca agctagaaaa    1020
aaaaagagct cgtcttgcta ctgttgttat actgctgttg cgttttctgt gtatgtgcgt    1080
ggatgtgtta gctgtatgct cttgttccag tgaggtgaac cgtggacatg ctggtgtggt    1140
gtccagaaag atatgctcaa agttcgctct gtaattttcg aaaaaaaaaa aaaaaaa      1197
```

<210> SEQ ID NO 3
<211> LENGTH: 310
<212> TYPE: PRT
<213> ORGANISM: Zea mays

<400> SEQUENCE: 3

```
Met Thr Ala Gly Gln Leu Leu Arg Thr Glu Pro Ser Ala Gln Pro Gln
 1               5                  10                  15

Arg Val Arg His Ser Thr Pro Pro Ala Ala Leu Gln Ala Asp Ile Val
                20                  25                  30

Pro Ser Tyr Pro Pro Pro Glu Ser Asp Gly Asp Glu Ser Trp Val Trp
            35                  40                  45

Ser Gln Ile Lys Ala Glu Ala Arg Arg Asp Ala Asp Ala Glu Pro Ala
        50                  55                  60

Leu Ala Ser Phe Leu Tyr Ala Thr Val Leu Ser His Ala Ser Leu Asp
 65                  70                  75                  80

Arg Ser Leu Ala Phe His Leu Ala Asn Lys Leu Cys Ser Ser Thr Leu
                85                  90                  95

Leu Ser Thr Leu Leu Tyr Asp Leu Phe Val Ala Ser Leu Ala Glu His
            100                 105                 110

Pro Ser Val Arg Ala Ala Ala Val Ala Asp Leu Ile Ala Ala Arg Ser
        115                 120                 125

Arg Asp Pro Ala Cys Ala Gly Phe Ala His Cys Leu Leu Asn Tyr Lys
    130                 135                 140

Gly Phe Leu Ala Val Gln Ala His Arg Val Ala His Val Leu Trp Ala
145                 150                 155                 160

Gln Gly Arg Arg Ala Leu Ala Leu Ala Leu Gln Ser Arg Val Ala Glu
                165                 170                 175

Val Phe Ala Val Asp Ile His Pro Ala Ala Thr Val Gly Arg Gly Ile
            180                 185                 190

Leu Leu Asp His Ala Thr Gly Val Val Val Gly Glu Thr Ala Val Val
        195                 200                 205

Gly Asp Asn Val Ser Ile Leu His His Val Thr Leu Gly Gly Thr Gly
    210                 215                 220

Lys Ala Val Gly Asp Arg His Pro Lys Ile Gly Asp Gly Val Leu Ile
225                 230                 235                 240

Gly Ala Gly Ala Thr Val Leu Gly Asn Val Arg Ile Gly Ala Gly Ala
                245                 250                 255

Lys Val Gly Ala Gly Ser Val Val Leu Ile Asp Val Pro Pro Arg Ser
            260                 265                 270

Thr Ala Val Gly Asn Pro Ala Arg Leu Ile Gly Gly Lys Lys Gly Glu
        275                 280                 285

Glu Val Met Pro Gly Glu Ser Met Asp His Thr Ser Phe Ile Gln Gln
```

-continued

```
                290                 295                 300
Trp Ser Asp Tyr Ile Ile
305                 310

<210> SEQ ID NO 4
<211> LENGTH: 1294
<212> TYPE: DNA
<213> ORGANISM: Triticum aestivum

<400> SEQUENCE: 4
gcccacacac ccacccacca gcagcaatcc atccatccct cgcagctccg gcggcgatgc      60
cggcgggcca gcagccaccg gcgcgcgagc ccgacggcgg cgactccaac caccaccccc     120
acccgccgcc ccccacgccc gcgctcccgt ccgaggtggt gccggcctac ccgccgccgg     180
agtcggagga cgacgagtcc tgggtgtgga cgcagatcaa ggcggaggcc cggcgcgacg     240
ccgacgccga gccggcgctc gcctccttcc tctacgccac ggtgctctcc cacccctccc     300
tgccccgctc cctctccttc cacctcgcca acaagctctg ctcctccacc ctcctctcca     360
cgctcctcta cgacctcttc ctcgcctccc tcaccgcgca cccctccctc cgcgccgccg     420
tcgtcgccga cctcctcgcc gcgcgcgccc gcgacccgc ctgcgtcgga ttctcccact      480
gcctcctcaa ctacaagggc ttcctcgcca tccaggcgca ccgcgtcgcg cacgtgctct     540
gggcgcagaa ccgccgcccg ctcgcgctcg ccctccagtc ccgcgtcgcc gacgtcttcg     600
ccgtcgacat ccaccccgcc gccgtcgtcg gcaaggccat cctcctcgac cacgccaccg     660
gcgtcgtcat cggggagacc gccgtcgtcg gtgacaacgt ctccatcctc caccacgtca     720
ccctgggtgg gactggcaag gcggtcggcg accgccaccc caagattggg gacggcgtgc     780
tcataggtgc cggcgccaca atcctcggca acgtcatgat ggagccgggg gccaagattg     840
gggctggctc cgtggtgctg atagatgtgc cggcgcggag cacggcggtg gggaaccctg     900
ccaggctcat cggagggagg aagggcgagt ccgacaagga cgaggacatg cccggagagt     960
ccatggatca cacctccttc atacggcagt ggtccgacta caccatctga gagagccatt    1020
gtccaaggtc tattactcat cctctgtatc agtaaccgtg ttgtgctacc aaatacgtag    1080 tgatttttgtt ttggtattgt tcgcttgtgg atgaacatca actgtagtct aatgtcaagt    1140
gtgtatggcc aattgtttct tcagctgagc gaccatgctc ggatactgat agtggatgat    1200
tgatcaatga ataattttgt gatctacaat ggatttggtt gtattttcaa tcatttgctg    1260
gattaaaaaa aaaaaaaaaa aaaaaaaaaa aaaa                                1294

<210> SEQ ID NO 5
<211> LENGTH: 317
<212> TYPE: PRT
<213> ORGANISM: Triticum aestivum

<400> SEQUENCE: 5

Met Pro Ala Gly Gln Gln Pro Pro Ala Arg Glu Pro Asp Gly Gly Asp
  1               5                  10                  15

Ser Asn His His Pro His Pro Pro Pro Thr Pro Ala Leu Pro Ser
             20                  25                  30

Glu Val Val Pro Ala Tyr Pro Pro Glu Ser Glu Asp Asp Glu Ser
         35                  40                  45

Trp Val Trp Thr Gln Ile Lys Ala Glu Ala Arg Arg Asp Ala Asp Ala
 50                  55                  60

Glu Pro Ala Leu Ala Ser Phe Leu Tyr Ala Thr Val Leu Ser His Pro
 65                  70                  75                  80
```

```
Ser Leu Pro Arg Ser Leu Ser Phe His Leu Ala Asn Lys Leu Cys Ser
                85                  90                  95

Ser Thr Leu Leu Ser Thr Leu Tyr Asp Leu Phe Leu Ala Ser Leu
            100                 105                 110

Thr Ala His Pro Ser Leu Arg Ala Ala Val Val Ala Asp Leu Leu Ala
            115                 120                 125

Ala Arg Ala Arg Asp Pro Ala Cys Val Gly Phe Ser His Cys Leu Leu
    130                 135                 140

Asn Tyr Lys Gly Phe Leu Ala Ile Gln Ala His Arg Val Ala His Val
145                 150                 155                 160

Leu Trp Ala Gln Asn Arg Arg Pro Leu Ala Leu Ala Leu Gln Ser Arg
                165                 170                 175

Val Ala Asp Val Phe Ala Val Asp Ile His Pro Ala Ala Val Val Gly
            180                 185                 190

Lys Ala Ile Leu Leu Asp His Ala Thr Gly Val Val Ile Gly Glu Thr
            195                 200                 205

Ala Val Val Gly Asp Asn Val Ser Ile Leu His His Val Thr Leu Gly
    210                 215                 220

Gly Thr Gly Lys Ala Val Gly Asp Arg His Pro Lys Ile Gly Asp Gly
225                 230                 235                 240

Val Leu Ile Gly Ala Gly Ala Thr Ile Leu Gly Asn Val Met Ile Gly
                245                 250                 255

Ala Gly Ala Lys Ile Gly Ala Gly Ser Val Val Leu Ile Asp Val Pro
            260                 265                 270

Ala Arg Ser Thr Ala Val Gly Asn Pro Ala Arg Leu Ile Gly Gly Arg
            275                 280                 285

Lys Gly Glu Ser Asp Lys Asp Glu Asp Met Pro Gly Glu Ser Met Asp
    290                 295                 300

His Thr Ser Phe Ile Arg Gln Trp Ser Asp Tyr Thr Ile
305                 310                 315

<210> SEQ ID NO 6
<211> LENGTH: 289
<212> TYPE: PRT
<213> ORGANISM: Allium cepa

<400> SEQUENCE: 6

Met Pro Cys Ser Thr Leu Pro Ile Pro Thr Phe Pro Pro Pro Glu Ser
1               5                   10                  15

Glu Ser Asp Glu Ser Trp Val Trp Asn Gln Ile Lys Ala Glu Ala His
            20                  25                  30

Arg Asp Ala Glu Ser Glu Pro Ala Leu Ala Ser Tyr Leu Tyr Ser Thr
        35                  40                  45

Ile Ile Ser His Pro Ser Leu Ala Arg Ser Leu Ser Phe His Leu Ala
    50                  55                  60

Asn Lys Leu Cys Ser Ser Thr Leu Leu Ser Thr Ser Leu Tyr Asp Leu
65                  70                  75                  80

Phe Leu Asn Thr Leu Ser Thr Phe Pro Thr Val Leu Ser Ala Ser Val
                85                  90                  95

Ala Asp Leu Ile Ala Ala Arg His Arg Asp Pro Ala Cys Val Gly Phe
            100                 105                 110

Ser His Cys Leu Leu Asn Phe Lys Gly Phe Leu Ala Val Gln Thr Gln
            115                 120                 125

Arg Ile Ala His Val Leu Trp Ser Gln Ser Arg Arg Pro Leu Ala Leu
```

```
                        130                 135                 140
Ala Leu His Ser Arg Val Ala Asp Val Leu Ser Val Asp Ile His Pro
145                 150                 155                 160

Ala Ala Arg Ile Gly Lys Gly Ile Leu Leu Asp His Ala Thr Gly Val
                165                 170                 175

Val Ile Gly Glu Thr Ala Val Ile Gly Asn Asn Val Ser Ile Leu His
            180                 185                 190

His Val Thr Leu Gly Gly Thr Gly Lys Ala Gly Gly Asp Arg His Pro
            195                 200                 205

Lys Ile Gly Asp Gly Val Leu Ile Gly Ala Gly Ala Thr Ile Leu Gly
        210                 215                 220

Asn Ile Arg Ile Gly Ala Gly Ala Lys Val Gly Ala Gly Ser Val Val
225                 230                 235                 240

Leu Ile Asp Val Pro Pro Arg Thr Thr Ala Val Gly Asn Pro Ala Arg
                245                 250                 255

Leu Ile Gly Gly Lys Glu Lys Pro Ser Val His Glu Asp Val Pro Gly
            260                 265                 270

Glu Ser Met Asp His Thr Ser Phe Ile Ser Glu Trp Ser Asp Tyr Ile
        275                 280                 285

Ile

<210> SEQ ID NO 7
<211> LENGTH: 294
<212> TYPE: PRT
<213> ORGANISM: Citrullus lanatus

<400> SEQUENCE: 7

Met Pro Val Gly Glu Leu Arg Phe Ser Ser Gln Ser Ser Thr Thr Val
 1               5                  10                  15

Val Glu Ser Thr Thr Asn Asn Asp Glu Thr Trp Leu Trp Gly Gln Ile
                20                  25                  30

Lys Ala Glu Ala Arg Arg Asp Ala Glu Ser Glu Pro Ala Leu Ala Ser
            35                  40                  45

Tyr Leu Tyr Ser Thr Ile Leu Ser His Ser Ser Leu Glu Arg Ser Leu
        50                  55                  60

Ser Phe His Leu Gly Asn Lys Leu Cys Ser Ser Thr Leu Leu Ser Thr
65                  70                  75                  80

Leu Leu Tyr Asp Leu Phe Leu Asn Ala Phe Ser Thr Asp Tyr Cys Leu
                85                  90                  95

Arg Ser Ala Val Val Ala Asp Leu Gln Ala Ala Arg Glu Arg Asp Pro
            100                 105                 110

Ala Cys Val Ser Phe Ser His Cys Leu Leu Asn Tyr Lys Gly Phe Leu
        115                 120                 125

Ala Cys Gln Ala His Arg Val Ala His Lys Leu Trp Asn Gln Ser Arg
130                 135                 140

Arg Pro Leu Ala Leu Ala Leu Gln Ser Arg Ile Ala Asp Val Phe Ala
145                 150                 155                 160

Val Asp Ile His Pro Ala Ala Arg Ile Gly Lys Gly Ile Leu Phe Asp
                165                 170                 175

His Ala Thr Gly Val Val Gly Glu Thr Ala Val Ile Gly Asn Asn
            180                 185                 190

Val Ser Ile Leu His His Val Thr Leu Gly Gly Thr Gly Lys Met Cys
        195                 200                 205

Gly Asp Arg His Pro Lys Ile Gly Asp Gly Val Leu Ile Gly Ala Gly
```

```
            210                 215                 220
Ala Thr Ile Leu Gly Asn Val Lys Ile Gly Glu Gly Ala Lys Ile Gly
225                 230                 235                 240

Ala Gly Ser Val Val Leu Ile Asp Val Pro Pro Arg Thr Thr Ala Val
                245                 250                 255

Gly Asn Pro Ala Arg Leu Val Gly Gly Lys Glu Lys Pro Ser Gln Leu
            260                 265                 270

Glu Asp Ile Pro Gly Glu Ser Met Asp His Thr Ser Phe Ile Ser Glu
            275                 280                 285

Trp Ser Asp Tyr Ile Ile
            290

<210> SEQ ID NO 8
<211> LENGTH: 289
<212> TYPE: PRT
<213> ORGANISM: Allium tuberosum

<400> SEQUENCE: 8

Met Pro Cys Ser Thr Val Pro Phe Pro Thr Phe Pro Pro Pro Glu Ser
  1               5                  10                  15

Glu Ser Asp Glu Ser Trp Val Trp Asn Gln Ile Lys Ala Glu Ala Arg
             20                  25                  30

Arg Asp Ala Glu Ser Glu Pro Ala Leu Ala Ser Tyr Leu Tyr Ser Thr
         35                  40                  45

Ile Ile Ser His Pro Ser Leu Ala Arg Ser Leu Ser Phe His Leu Ala
     50                  55                  60

Asn Lys Leu Cys Ser Ser Thr Leu Leu Ser Thr Ser Leu Tyr Asp Leu
 65                  70                  75                  80

Phe Leu Asn Ala Leu Ser Thr Phe Pro Thr Ile Leu Ser Ala Thr Val
                 85                  90                  95

Ala Asp Leu Ile Ala Ala Arg His Arg Asp Pro Ala Cys Ile Gly Phe
            100                 105                 110

Ser His Cys Leu Leu Asn Phe Lys Gly Phe Leu Ala Val Gln Thr Gln
        115                 120                 125

Arg Ile Ala His Val Leu Trp Ser Gln Ser Arg Arg Pro Leu Ala Leu
130                 135                 140

Ala Leu His Ser Arg Val Ala Asp Val Leu Ser Val Asp Ile His Pro
145                 150                 155                 160

Ala Ala Arg Ile Gly Lys Gly Ile Leu Leu Asp His Ala Thr Gly Val
                165                 170                 175

Val Ile Gly Glu Thr Ala Val Ile Gly Asn Asn Val Ser Ile Leu His
            180                 185                 190

His Val Thr Leu Gly Gly Thr Gly Lys Ala Gly Gly Asp Arg His Pro
        195                 200                 205

Lys Ile Gly Asp Gly Val Leu Ile Gly Ala Gly Ala Thr Ile Leu Gly
    210                 215                 220

Asn Ile Arg Ile Gly Ala Gly Ala Lys Ile Gly Ala Gly Ser Val Val
225                 230                 235                 240

Leu Ile Asp Val Pro Pro Arg Thr Thr Ala Val Gly Asn Pro Ala Arg
                245                 250                 255

Leu Ile Gly Gly Lys Glu Lys Pro Ser Met His Glu Asp Val Pro Gly
            260                 265                 270

Glu Ser Met Asp His Thr Ser Phe Ile Ser Glu Trp Ser Asp Tyr Ile
        275                 280                 285
```

-continued

Ile

<210> SEQ ID NO 9
<211> LENGTH: 312
<212> TYPE: PRT
<213> ORGANISM: Arabidopsis thaliana

<400> SEQUENCE: 9

```
Met Pro Pro Ala Gly Glu Leu Arg His Gln Ser Pro Ser Lys Glu Lys
  1               5                  10                  15

Leu Ser Ser Val Thr Gln Ser Asp Glu Ala Glu Ala Ala Ser Ala Ala
                 20                  25                  30

Ile Ser Ala Ala Ala Ala Asp Ala Glu Ala Ala Gly Leu Trp Thr Gln
             35                  40                  45

Ile Lys Ala Glu Ala Arg Arg Asp Ala Glu Ala Glu Pro Ala Leu Ala
         50                  55                  60

Ser Tyr Leu Tyr Ser Thr Ile Leu Ser His Ser Ser Leu Glu Arg Ser
 65                  70                  75                  80

Ile Ser Phe His Leu Gly Asn Lys Leu Cys Ser Ser Thr Leu Leu Ser
                 85                  90                  95

Thr Leu Leu Tyr Asp Leu Phe Leu Asn Thr Phe Ser Ser Asp Pro Ser
                100                 105                 110

Leu Arg Asn Ala Thr Val Ala Asp Leu Arg Ala Ala Arg Val Arg Asp
            115                 120                 125

Pro Ala Cys Ile Ser Phe Ser His Cys Leu Leu Asn Tyr Lys Gly Phe
        130                 135                 140

Leu Ala Ile Gln Ala His Arg Val Ser His Lys Leu Trp Thr Gln Ser
145                 150                 155                 160

Arg Lys Pro Leu Ala Leu Ala Leu His Ser Arg Ile Ser Asp Val Phe
                165                 170                 175

Ala Val Asp Ile His Pro Ala Ala Lys Ile Gly Lys Gly Ile Leu Leu
            180                 185                 190

Asp His Ala Thr Gly Val Val Val Gly Glu Thr Ala Val Ile Gly Asn
        195                 200                 205

Asn Val Ser Ile Leu His His Val Thr Leu Gly Gly Thr Gly Lys Ala
    210                 215                 220

Cys Gly Asp Arg His Pro Lys Ile Gly Asp Gly Cys Leu Ile Gly Ala
225                 230                 235                 240

Gly Ala Thr Ile Leu Gly Asn Val Lys Ile Gly Ala Gly Ala Lys Val
                245                 250                 255

Gly Ala Gly Ser Val Val Leu Ile Asp Val Pro Cys Arg Gly Thr Ala
            260                 265                 270

Val Gly Asn Pro Ala Arg Leu Val Gly Gly Lys Glu Lys Pro Thr Ile
        275                 280                 285

His Asp Glu Glu Cys Pro Gly Glu Ser Met Asp His Thr Ser Phe Ile
    290                 295                 300

Ser Glu Trp Ser Asp Tyr Ile Ile
305                 310
```

SERINE O-ACETYTRANSFERASE

This application claims the benefit of U.S. Provisional Application No. 60/292,411, filed May 21, 2001, the entire content of which is herein incorporated by reference.

FIELD OF THE INVENTION

This invention is in the field of plant molecular biology. More specifically, this invention pertains to nucleic acid fragments encoding serine O-acetyltransferase in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include high affinity sulfate transporter and low affinity sulfate transporter proteins which serve to transport sulfur from the outside environment across the cell membrane into the cell (Smith et al. (1995) *PNAS* 92(20): 9373–9377). Once sulfur is in the cell, sulfate adenylyltransferase (ATP sulfurylase) (Bolchia et al. (1999) *Plant Mol. Biol.* 39(3):527–537) catalyzes the first step in assimilation, converting the inorganic sulfur into an organic form, adenosine-5' phosphosulfate (APS). Next, several enzymes further modify organic sulfur for use in the biosynthesis of cysteine and methionine. For example, adenylylsulfate kinase (APS kinase) catalyzes the conversion of APS to the biosynthetic intermediate PAPS (3'-phosphoadenosine-5' phosphosulfate) (Arz et al. (1994) *Biochim. Biophy. Acta* 1218(3):447–452). APS reductase (5' adenylyl phosphosulphate reductase) is utilized in an alternative pathway, resulting in an inorganic but cellularly bound (bound to a carrier) form of sulfur (sulfite) (Setya et al. (1996) *PNAS* 93(23):13383–13388). Sulfite reductase further reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakakibara et al. (1998) *J. Biol. Chem.* 124(3):615–621 and Saito et al. (1995) *J. Biol. Chem.* 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increased levels of these amino acids, which now often must be added a supplements to animal feed.

SUMMARY OF THE INVENTION

The present invention concerns isolated polynucleotides comprising a nucleotide sequence encoding a polypeptide having serine O-acetyltransferase activity wherein the amino acid sequence of the polypeptide and the amino acid sequence of SEQ ID NO:3 have at least 90% sequence identity, or wherein the amino acid sequence of the polypeptide and the amino acid sequence of SEQ ID NO:5 have at least 85% sequence identity. It is preferred that the sequence identity to SEQ ID NO:5 be at least 90%, it is more preferred that the sequence identity to SEQ ID NO:3 or to SEQ ID NO:5 be at least 95%. The present invention also relates to isolated polynucleotides comprising the complement of the nucleotide sequence. More specifically, the present invention concerns isolated polynucleotides encoding the polypeptide sequence of SEQ ID NO:3 or SEQ ID NO:5 or nucleotide sequences comprising the nucleotide sequence of SEQ ID NO:1, SEQ ID NO:2 or SEQ ID NO:4.

In a first embodiment, the present invention relates to an isolated polynucleotide comprising: (a) a first nucleotide sequence encoding a first polypeptide comprising at least 200 amino acids, wherein the amino acid sequence of the first polypeptide and the amino acid sequence of SEQ ID NO:3 have at least 90% or 95% sequence identity based on the ClustalV alignment method, (b) a second nucleotide sequence encoding a second polypeptide comprising at least 250 amino acids, wherein the amino acid sequence of the second polypeptide and the amino acid sequence of SEQ ID NO:5 have at least 85%, 90% or 95% sequence identity based on the ClustalV alignment method, or (c) the complement of the first or second nucleotide sequence, wherein the complement and the first or second nucleotide sequence contain the same number of nucleotides and are 100% complementary in a pairwise alignment. The first polypeptide preferably comprises the amino acid sequence of SEQ ID NO:3, and the second polypeptide preferably comprises the amino acid sequence of SEQ ID NO:5. The first nucleotide sequence preferably comprises the nucleotide sequence of SEQ ID NO:1 or SEQ ID NO:2, and the second nucleotide sequence preferably comprises the nucleotide sequence of SEQ ID NO:4. The polypeptide preferably has serine O-acetyltransferase activity.

In a second embodiment, the present invention concerns a recombinant DNA construct comprising any of the isolated polynucleotides of the present invention operably linked to at least one regulatory sequence, and a cell, a plant, and a seed comprising the recombinant DNA construct.

In a third embodiment, the present invention relates to a vector comprising any of the isolated polynucleotides of the present invention.

In a fourth embodiment, the present invention concerns an isolated polynucleotide comprising a nucleotide sequence comprised by any of the polynucleotides of the first embodiment, wherein the nucleotide sequence contains at least 30, 40, or 60 nucleotides.

In a fifth embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In a sixth embodiment, the present invention concerns a method for producing a transgenic plant comprising transforming a plant cell with any of the isolated polynucleotides of the present invention and regenerating a plant from the transformed plant cell. The invention is also directed to the transgenic plant produced by this method, and seed obtained from this transgenic plant.

In a seventh embodiment, the present invention relates to an isolated polypeptide comprising: (a) a first amino acid sequence comprising at least 200 amino acids, wherein the first amino acid sequence and the amino acid sequence of SEQ ID NO:3 have at least 90% or 95% sequence identity based on the ClustalV alignment method, or (b) a second amino acid sequence comprising at least 250 amino acids, wherein the second amino acid sequence and the amino acid sequence of SEQ ID NO:5 have at least 85%, 90%, or 95% sequence identity based on the ClustalV alignment method. The first amino acid sequence preferably comprises the amino acid sequence of SEQ ID NO:3, and the second amino acid sequence preferably comprises the amino acid sequence of SEQ ID NO:5. The polypeptide preferably has serine O-acetyltransferase activity.

In an eighth embodiment, the invention concerns a method for isolating a polypeptide encoded by the polynucleotide of the present invention comprising isolating the polypeptide from a cell containing a recombinant DNA construct comprising the polynucleotide operably linked to at least one regulatory sequence.

In a ninth embodiment, the present invention relates to a virus, preferably a baculovirus, comprising any of the isolated polynucleotides of the present invention or any of the recombinant DNA constructs of the present invention.

In a tenth embodiment, the invention concerns a method of selecting an isolated polynucleotide that affects the level of expression of a gene encoding a serine O-acetyltransferase protein or activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of serine O-acetyltransferase protein or activity in the host cell containing the isolated polynucleotide; and (d) comparing the level of serine O-acetyltransferase protein or activity in the host cell containing the isolated polynucleotide with the level of serine O-acetyltransferase protein or activity in the host cell that does not contain the isolated polynucleotide.

In an eleventh embodiment, the invention relates to a method of obtaining a nucleic acid fragment encoding a substantial portion of a serine O-acetyltransferase protein, preferably a plant serine O-acetyltransferase protein comprising the steps of: synthesizing an oligonucleotide primer comprising a nucleotide sequence of at least 30 (preferably at least 40, most preferably at least 60) contiguous nucleotides derived from a nucleotide sequence of SEQ ID NO:1, SEQ ID NO:2 or SEQ ID NO:4, and the complement of such nucleotide sequences; and amplifying a nucleic acid fragment (preferably a cDNA inserted in a cloning vector) using the oligonucleotide primer. The amplified nucleic acid fragment preferably will encode a substantial portion of a serine O-acetyltransferase protein amino acid sequence.

In a twelfth embodiment, this invention concerns a method of obtaining a nucleic acid fragment encoding all or a substantial portion of the amino acid sequence encoding a serine O-acetyltransferase protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

In a thirteenth embodiment, this invention relates a method for positive selection of a transformed cell comprising: (a) transforming a host cell with the recombinant DNA construct of the present invention or an expression cassette of the present invention; and (b) growing the transformed host cell, preferably a plant cell, such as a monocot or a dicot, under conditions which allow expression of the serine O-acetyltransferase polynucleotide in an amount sufficient to complement a null mutant to provide a positive selection means.

In a fourteenth embodiment, this invention concerns a method of altering the level of expression of a serine O-acetyltransferase protein in a host cell comprising: (a) transforming a host cell with a recombinant DNA construct of the present invention; and (b) growing the transformed host cell under conditions that are suitable for expression of the recombinant DNA construct wherein expression of the recombinant DNA construct results in production of altered levels of the serine O-acetyltransferase protein in the transformed host cell.

BRIEF DESCRIPTION OF THE DRAWING AND SEQUENCE LISTINGS

The invention can be more fully understood from the following detailed description and the accompanying drawing and Sequence Listing which form a part of this application.

FIG. 1 (FIGS. 1A and 1B) depicts the amino acid sequence alignment between the serine O-acetyltransferase from corn (SEQ ID NO:3) encoded by the nucleotide sequences derived from corn clone cr1n.pk0085.c5 (SEQ ID NO:1) or corn clone p0022.cglnf80r (SEQ ID NO:2), the wheat serine O-acetyltransferase (SEQ ID NO:5) encoded by the nucleotide sequence of wheat clone wpa1c.pk015.c12 (SEQ ID NO:4), the serine O-acetyltransferase from *Allium tuberosum* (NCBI GenBank Identifier (GI) No. 7384806; SEQ ID NO:8), and the serine O-acetyltransferase, SAT-52, from *Arabidopsis thaliana* (NCBI GI No. 2146774; SEQ ID NO:9). Amino acids which are identical among all four sequences at a given position in the consensus sequence are indicated with an asterisk (*). Dashes are used by the program to maximize alignment of the sequences. The amino acid residues for each sequence are numbered to the left of each line of sequence, and to the right of the last line of sequence. The amino acid residues of the consensus sequence are numbered below each group of sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| | Serine O-Acetyltransferase | | |
|---|---|---|---|
| | | SEQ ID NO: | |
| Plant | Clone Designation | (Nucleotide) | (Amino Acid) |
| Corn | cr1n.pk0085.c5 | 1 | 3 |
| Corn | p0022.cglnf80r | 2 | 3 |
| Wheat | wpa1c.pk015.c12 | 4 | 5 |

The amino acid sequence of SEQ ID NO:3 is encoded by nucleotides number 49 to 978 of SEQ ID NO:1 and also by nucleotides number 71 to 1000 of SEQ ID NO:2.

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

The problem to be solved was to identify polynucleotides that encode serine O-acetyltransferase proteins. These polynucleotides may be used in plant cells to alter sulfur assimilation and the biosynthesis of cysteine and methionine. More specifically, the polynucleotides of the instant invention may be used to create transgenic plants where the serine O-acetyltransferase levels are altered with respect to non-transgenic plants which would result in plants with increased levels of cysteine and methionine. The present invention has solved this problem by providing polynucleotide and deduced polypeptide sequences corresponding to novel serine O-acetyltransferase proteins from corn (*Zea mays*) and wheat (*Triticum aestivum*).

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1, SEQ ID NO:2 or SEQ ID NO:4, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NOs:1, 2 or 4, and the complement of such nucleotide sequences may be used to affect the expression and/or function of a serine O-acetyltransferase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol* 215:403–410; see also the explanation of the BLAST algorithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) Biochemistry of Plants 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632). A "mitochondrial signal peptide" is an amino acid sequence which directs a precursor protein into the mitochondria (Zhang and Glaser (2002) Trends Plant Sci 7:14–21).

"Transformation" refers to the transfer of a nucleic acid fragment into the genome of a host organism. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277; Ishida Y. et al. (1996) Nature Biotech. 14:745–750) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

The present invention concerns an isolated polynucleotide comprising a nucleotide sequence encoding a serine O-acetyltransferase polypeptide having at least 90% sequence identity, based on the ClustalV alignment method, when compared to the amino acid sequence of SEQ ID NO:3, or having at least 85% sequence identity, based on the ClustalV alignment method, when compared to the amino acid sequence of SEQ ID NO:5. The nucleotide sequence of the isolated polynucleotide preferably comprises the nucleotide sequence of SEQ ID NOs:1, 2 or 4.

This invention also relates to the isolated complement of such polynucleotides, wherein the complement and the polynucleotide consist of the same number of nucleotides, and the nucleotide sequences of the complement and the polynucleotide have 100% complementarity in a pairwise alignment.

Nucleic acid fragments encoding at least a portion of several serine O-acetyltransferase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other serine O-acetyltransferase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NOs:1, 2 or 4 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of serine O-acetyltransferase in those cells. Serine O-acetyltransferase activity can be determined by the methods described in Urano et al. (2000) *Gene* 257:269–277, and in PCT International Publication Number WO 00/36127. Serine O-acetyltransferase is involved in sulfate assimilation and the pathway leading to cysteine biosynthesis, which in turn serves as an organic sulfur donor for multiple other pathways in the cell, including methionine biosynthesis. This enzyme and the gene(s) that encodes the protein have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as chloroplast transit sequences (Keegstra (1989) Cell 56:247–253), signal sequences or sequences encoding endoplasmic reticulum localization (Chrispeels (1991) Ann. Rev. Plant Phys. Plant Mol. Biol. 42:21–53), nuclear localization signals (Raikhel (1992) Plant Phys. 100:1627–1632) or mitochondrial signal sequences (Zhang and Glaser (2002) Trends Plant Sci 7:14–21) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another embodiment, the present invention concerns a serine O-acetyltransferase polypeptide having an amino acid sequence that is at least 90% identical, based on the ClustalV method of alignment, to the amino acid sequence of SEQ ID NO:3, or having an amino acid sequence that is at least 85% identical, based on the ClustalV method of alignment, to the amino acid sequence of SEQ ID NO:5. The amino acid sequence of the serine O-acetyltransferase preferably comprises the amino acid sequence of SEQ ID NO:3 or SEQ ID NO:5.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded serine O-acetyltransferase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) Genomics 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) Am. J. Hum. Genet. 32:314–331).

The production and use of plant gene-derived probes for use in genetic mapping is described in Bernatzky and Tanksley (1986) Plant Mol. Biol. Reporter 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various corn (*Zea mays*) and wheat (*Triticum aestivum*) tissues were prepared. The characteristics of the libraries are described below.

TABLE 2 cDNA Libraries from Corn and Wheat

| Library | Tissue | Clone |
|---|---|---|
| cr1n | Corn Root From 7 Day Old Seedlings* | cr1n.pk0085.c5 |
| p0022 | Corn Mid Rib of the Middle ¾ of the 3rd Leaf Blade from Green Leaves Treated with Jasmonic Acid (1 mg/ml in 0.02% Tween 20) 24 Hours Before Collection* | p0022.cglnf80r |
| wpa1c | Wheat Pre-meiotic Anther | wpa1c.pk015.c12 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis.

Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding serine O-acetyltransferase were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Serine O-Acetyltransferase

The BLASTX search using the EST sequences from clones listed in Table 3 revealed similarity of the polypeptides encoded by the cDNAs to serine O-acetyltransferases from *Allium cepa* (NCBI GI No. 6601494; SEQ ID NO:6), *Citrullus lanatus* (NCBI GI No. 1361979; SEQ ID NO:7) and *Allium tuberosum* (NCBI GenBank Identifier (GI) No.

7384806; SEQ ID NO:8). Shown in Table 3 are the BLAST results for individual EST sequences ("EST"), the sequences of the entire cDNA inserts comprising the indicated cDNA clones ("FIS"), the sequences of contigs assembled from two or more EST, FIS or PCR sequences ("Contig"), or sequences encoding an entire protein derived from an FIS or contig ("CGS"):

TABLE 3

BLAST Results for Sequences Encoding Polypeptides Homologous to Serine O-Acetyltransferase

| Clone | Status | BLAST Results NCBI GI No. | pLog Score |
|---|---|---|---|
| cr1n.pk0085.c5 (FIS) | CGS | 1361979 | 122.00 |
| p0022.cglnf80r (FIS) | CGS | 6601494 | 129.00 |
| wpa1c.pk015.c12 (FIS) | CGS | 7384806 | 131.00 |

PCT Publication WO 00/04167 which published Jan. 27, 2000 describes the isolation and initial characterization of clones cr1n.pk0085.c5 and p0022.cglnf80r but does not disclose the sequence of the entire cDNA inserts contained in these clones.

FIG. 1 depicts the amino acid sequence alignment between the serine O-acetyltransferase from corn (SEQ ID NO:3) encoded by the nucleotide sequences derived from corn clone cr1n.pk0085.c5 (nucleotides 49 to 978 of SEQ ID NO:1) or corn clone p0022.cglnf80r (nucleotides 71 to 1000 of SEQ ID NO:2), the wheat serine O-acetyltransferase (SEQ ID NO:5) encoded by the nucleotide sequence of wheat clone wpa1c.pk015.c12 (nucleotides 57 to 1007 of SEQ ID NO:4), the serine O-acetyltransferase from *Allium tuberosum* (NCBI GenBank Identifier (GI) No. 7384806; SEQ ID NO:8), and the serine O-acetyltransferase, SAT-52, from *Arabidopsis thaliana* (NCBI GI No. 2146774; SEQ ID NO:9). Amino acids which are identical among all four sequences at a given position in the consensus sequence are indicated with an asterisk (*).

The data in Table 4 represents a calculation of the percent identity of the amino acid sequences set forth in SEQ ID NO:3 and SEQ ID NO:5, compared to *Allium tuberosum* (NCBI GenBank Identifier (GI) No. 7384806; SEQ ID NO:8), and five serine O-acetyltransferase proteins from *Arabidopsis thaliana* (PCT International Publication Number WO 00/36127). Also listed are the cellular locations for the different serine O-acetyltransferase proteins. The polypeptides of SEQ ID NO:3 and SEQ ID NO:5 are most similar to the *Allium tuberosum* cytosolic serine O-acetyltransferase and the *Arabidopsis thaliana* cytosolic serine O-acetyltransferase, SAT52. The cytosolic nature of the polypeptides of SEQ ID NO:3 and SEQ ID NO:5 is further indicated by the conservation of sequence identity at the carboxy terminus (FIG. 1; Urano et al. (2000) Gene 257:269–277).

TABLE 4

Percent Identity of Amino Acid Sequences Deduced From the Nucleotide Sequences of cDNA Clones Encoding Polypeptides Homologous to Serine O-Acetyltransferase

| Homologous Protein | GI No. | Cellular Location | % Identity to SEQ ID NO: 3 | % Identity to SEQ ID NO: 5 |
|---|---|---|---|---|
| *A. tuberosum* | 7384806 | cytosol | 75.1 | 77.2 |
| Arabidopsis SAT52 | 2146774 | cytosol | 68.1 | 70.2 |

TABLE 4-continued

Percent Identity of Amino Acid Sequences Deduced From the Nucleotide Sequences of cDNA Clones Encoding Polypeptides Homologous to Serine O-Acetyltransferase

| Homologous Protein | GI No. | Cellular Location | % Identity to SEQ ID NO: 3 | % Identity to SEQ ID NO: 5 |
|---|---|---|---|---|
| Arabidopsis SAT3 | 608577 | cytosol | 51.6 | 51.3 |
| Arabidopsis SAT2 | 5597011 | chloroplast | 45.8 | 44.2 |
| Arabidopsis SAT4 | 17225592 | chloroplast | 47.1 | 46.7 |
| Arabidopsis SAT1 | 1184048 | mitochondria | 50.6 | 50.8 |

Sequence alignments and percent identity calculations were performed using the Megalign program of the LASERGENE bioinformatics computing suite (DNASTAR Inc., Madison, Wis.). Multiple alignment of the sequences was performed using the ClustalV method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode serine O-acetyltransferase proteins.

Example 4

Expression of Recombinant DNA Constructs in Monocot Cells

A recombinant DNA construct comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptide, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptide. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/IL), 20 μL spermidine (0.1 M), and 50 μL CaCl₂ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 μg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 μL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Serine O-acetyltransferase activity can be determined by the methods described in Urano et al. (2000) Gene 257:269–277, and in PCT International Publication Number WO 00/36127.

What is claimed is:

1. An isolated polynucleotide comprising:
   (a) a nucleotide sequence encoding a polypeptide having serine O-acetyltransferase activity, wherein the polypeptide has an amino acid sequence of at least 90% sequence identity, based on the Clustal V method of alignment, when compared to SEQ ID NO:3, or a complement of the nucleotide sequence, wherein the complement and the nucleotide sequence consist of the same number of nucleotides and are 100% complementary.

2. The polynucleotide of claim 1, wherein the amino acid sequence of the polypeptide has at least 95% sequence identity, based on the Clustal V method of alignment, when compared to SEQ ID NO:3.

3. The polynucleotide of claim 1, wherein the amino acid sequence of the polypeptide comprises SEQ ID NO:3.

4. The polynucleotide of claim 1, wherein the nucleotide sequence comprises SEQ ID NO:1 or SEQ ID NO:2.

5. A vector comprising the polynucleotide of claim 1.

6. A recombinant DNA construct comprising the polynucleotide of claim 1 operably linked to at least one regulatory sequence.

7. A method for tranrforming a cell, comprising transforming a cell with the polynucleotide of claim 1.

8. A cell comprising the recombinant DNA construct of claim 6.

9. A method for producing a plant comprising transforming a plant cell with the recombinant DNA construct of claim 6 and regenerating a plant from the transformed plant cell.

10. A plant comprising the recombinant DNA construct of claim 6.

11. A seed comprising the recombinant DNA construct of claim 6.

* * * * *